(12) United States Patent
Sanderson

(10) Patent No.: US 7,608,985 B2
(45) Date of Patent: Oct. 27, 2009

(54) METHOD OF DETECTING ACCELERATION IN VEHICLES

(75) Inventor: Terry M. Sanderson, Tucson, AZ (US)

(73) Assignee: Raytheon Company, Waltham, MA (US)

( * ) Notice: Subject to any disclaimer, the term of this patent is extended or adjusted under 35 U.S.C. 154(b) by 0 days.

(21) Appl. No.: 12/185,246

(22) Filed: Aug. 4, 2008

(65) Prior Publication Data

US 2008/0309195 A1    Dec. 18, 2008

Related U.S. Application Data

(62) Division of application No. 11/668,544, filed on Jan. 30, 2007, now Pat. No. 7,411,338.

(51) Int. Cl.
*H01L 41/113*    (2006.01)

(52) U.S. Cl. .................. 310/338; 310/319; 73/493; 73/514.01; 73/514.39

(58) Field of Classification Search .................. 310/319, 310/336, 338, 339
See application file for complete search history.

(56) References Cited

U.S. PATENT DOCUMENTS

| | | | |
|---|---|---|---|
| 3,493,986 A | 2/1970 | Erwin | |
| 4,833,360 A | 5/1989 | Holly | |
| 4,944,185 A | 7/1990 | Clark, Jr. et al. | |
| 5,679,888 A * | 10/1997 | Tohda et al. | 73/105 |
| 6,277,299 B1 | 8/2001 | Seyed-Bolorforosh | |
| 6,992,423 B2 | 1/2006 | Mancosu et al. | |
| 7,411,338 B1 * | 8/2008 | Sanderson | 310/339 |
| 7,467,558 B2 * | 12/2008 | Fukuda et al. | 73/862.68 |
| 2002/0127384 A1 | 9/2002 | Mulligan et al. | |
| 2004/0020296 A1 | 2/2004 | Moles et al. | |
| 2006/0012282 A1 * | 1/2006 | Nanataki et al. | 313/311 |
| 2006/0250067 A1 * | 11/2006 | Nanataki et al. | 313/311 |
| 2008/0066564 A1 * | 3/2008 | Hayakawa et al. | 73/862.628 |

OTHER PUBLICATIONS

Giurgiutiu, Victor, PhD. et al., "In-situ Fabricated Smart Material Active Sensors for Structural Health Monitoring", Smart Materials III, pp. 68-78, Proceedings of SPIE, vol. 5648, 2005, Bellingham, Washington.

Sanderson, Terry, "Thermoelastic Modeling of Laser Generated Ultrasound for Nondestructive Materials Testing", PhD. Thesis (1997).

Yu, Lingyu, PhD. et al., "Advanced Signal Processing Techniques for Multi-Damage Detection with an Improved Embedded Ultrasonic Structural Radar Algorithm and Piezoelectric Wafer Active Sensors", 2004 ASME International Mechanical Engineering Congress and Exposition, Proceedings of IMECE04, (2004), pp. 47-52, Anaheim, California.

Giurgiutiu, Victor, PhD. et al., "Disbond detection with piezoelectric wafer active sensors in RC structures strengthened with FRP composite overlays", Earthquake Engineering and Engineering Vibration, (2003), vol. 2, No. 2, pp. 213-223.

(Continued)

*Primary Examiner*—Thomas M Dougherty
(74) *Attorney, Agent, or Firm*—Renner, Otto, Boisselle & Sklar, LLP

(57) ABSTRACT

Piezomagnetic, magneto-strictive, or electro-strictive material particles may also be distributed throughout the structural material of the structural member, which serve to amplify and otherwise enhance the signals from the piezoelectric material particles. The piezoelectric, electro-strictive, magneto-strictive, and/or piezomagnetic material particles may allow the structural member to exhibit an electrical and/or magnetic response to forces on the structural member, such as accelerations. This may allow the structural member to function as a force sensor or an accelerometer. Signals induced by such external forces or accelerations may be taken from the conductive pickups and used for various operations, for example, for arming a warhead of a missile or for triggering passenger safety features such as air bags in automobiles.

20 Claims, 1 Drawing Sheet

OTHER PUBLICATIONS

Giurgiutiu, Victor, PhD., "Tuned Lamb Wave Excitation and Detection with Piezoelectric Wafer Active Sensors for Structural Health Monitoring", Journal of Intelligent Material Systems and Structures, (2005), vol. 16, pp. 291-305.

Giurgiutiu, Victor, PhD., "Embedded Ultrasonics with Piezoelectric Wafer Active Sensors for Structural Health Monitoring of Thin-Wall Structures", 2003 ASME International Mechanical Engineering Congress, Proceedings of IMECE 2003, (2003), pp. 1-9, Washington, DC.

Liu, Weiping et al., "Automation of Data Collection for PWAS-based Structural Health Monitoring" Smart Structures and Materials, (2005) vol. 5765, pp. 1139-1147.

Doane, James et al., "An Initial Investigation of the Large Strain and Fatigue Loading Behavior of Piezoelectric Wafer Active Sensors", Smart Structures and Materials, (2005), vol. 5765, pp. 1148-1159.

Xu, Buli et al., "Efficient Electromechanical (E/M) Impedance Measuring Method for Active Sensor Structural Health Monitoring", Smart Structures and Materials, (2005), vol. 5765, pp. 271-280.

Giurgiutiu, Victor, PhD. et al., "Embedded Ultrasonic Structural Radar with Piezoelectric Wafer Active Sensors for Damage Detection in Cylindrical Shell Structures", American Institute of Aeronautics and Astronautics, (2004), Paper # AIAA-2004-1983, pp. 1-14.

Lin, Bin et al., "Review of In-situ Fabrication Methods of Piezoelectric Wafer Active Sensor for Sensing and Actuation Applications", Smart Structures and Materials, (2005), vol. 5765, pp. 1033-1044.

Jenkins, Christopher, "Development of Specifications for an Integrated Piezoelectric Wafer Active Sensors System", Smart Structures and Materials, (2005), vol. 5764, pp. 509-521.

Li, Zongjin et al., "Cement-Based 0-3 Piezoelectric Composites", Journal of the American Ceramic Society, American Ceramic Soc USA, (2002), XP-002480264, vol. 85, No. 2, pp. 305-313.

Rogers, Craig A. et al., "Smart Materials for Civil Engineering Applications", Emerging Materials for Civil Infrastructure: State of the Art, (2000), XP-002480263, pp. 1-40.

Ohara, Yoshinobu et al., "PZT-Polymer Piezoelectric Composites: A Design for an Acceleration Sensor", Sensors and Actuators, (1993), XP-00363159, vol. A36, No. 2, pp. 121-126.

* cited by examiner

METHOD OF DETECTING ACCELERATION IN VEHICLES

The application is a divisional of U.S. patent application Ser. No. 11/668,544, titled "Structural Material With Piezoelectric Material Particles," filed Jan. 30, 2007, now U.S. Pat. No. 7,411,338, the entire disclosure of which is incorporated herein by reference.

BACKGROUND OF THE INVENTION

1. Field of the Invention

The invention relates to structural materials and methods used in the general areas of quality and nondestructive testing, structural health monitoring, and detection of forces.

2. Description of the Related Art

Ultrasonic testing and vibrational resonance techniques are commonly used nondestructive techniques to test the integrity of polymer matrix composite structures and other structures. These techniques may be used to perform quality control tests at the time of manufacture, and/or structural health monitoring tests over the life of the structure. Piezoelectric transducers have been placed on such materials to both generate and receive ultrasonic and vibrational signals.

Ultrasonic testing techniques may employ longitudinal, shear, or surface waves. Defects existing in the structure may cause an irregularity in the ultrasonic signal, if the defect is located in an area probed by the ultrasonic signal. Defects in the structure may also alter its vibrational resonance response, if the defects are located in an area that is probed by the vibrational signal introduced into the structure.

For nondestructive quality control testing, skilled and expensive technicians have been needed to properly perform ultrasonic scans. Such ultrasonic testing is often a time consuming operation that slows down production. Vibrational resonance techniques have not been as commonly used, due to the expense and complexity of developing the necessary experimental apparatus. The ultrasonic method in particular suffers from the drawback that it is directional. Thus only limited parts of the structure may be examined at any one time. Full characterization of a structure, especially a complex structure, is a difficult, time-consuming, and expensive operation.

In large structures, such as those used on aircraft and bridges, piezoelectric wafer active sensors have been utilized. Piezoelectric wafer active sensors are flat, rectangular sensors made of ceramic material. The sensors are bonded to the structure, and their response over time is examined as part of a structural health monitoring operation. One problem with piezoelectric wafer active sensors is that they must be bonded to the structure, and the bond is prone to break down over time. Another problem is that such sensors do not easily conform to curved surfaces, and are easily broken. They may also produce unacceptable irregularities on aerodynamic surfaces, or they may detract from the aesthetic appeal of other structures.

From the foregoing it will be appreciated that improvements of this area of endeavor would be welcome.

SUMMARY OF THE INVENTION

According to an aspect of the invention, a load-bearing structural member is made of a continuous structural material with a plurality of piezoelectric material particles distributed in continuous structural material.

According to another aspect of the invention, a structure includes: a load-bearing structural member that includes a continuous structural material and a plurality of piezoelectric material particles distributed within the continuous structural material; and at least one conductive pickup attached to the structural member and operatively coupled to the piezoelectric material particles.

According to yet another aspect of the invention, a method of evaluating structural soundness of a structural member includes the steps of: placing at least one conductive pickup on the structural member, wherein the structural member includes a continuous structural material and a plurality of piezoelectric material particles in the continuous structural material; exciting at least some of the piezoelectric material particles; receiving electrical signals from the at least one conductive pickup, wherein the signals are at least in part caused by excitation of the piezoelectric material particles; and interpreting the signals to determine the structural soundness of the structural member.

According to still another aspect of the invention, a method of detecting acceleration in a vehicle includes the steps of: placing at least one conductive pickup on a structural member of the vehicle, wherein the structural member includes a continuous structural material, and a plurality of piezoelectric material particles in the continuous structural material; and receiving electrical signals from the at least one conductive pickup, wherein the signals are indicative of electrical fields in the structural member caused by stresses induced in the structural member by acceleration of the vehicle.

To the accomplishment of the foregoing and related ends, the invention comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

In the annexed drawings, which are not necessarily to scale.

DETAILED DESCRIPTION

A load-bearing structural member has a continuous structural material with piezoelectric material particles mixed in throughout. The structural material may be any of a variety of suitable materials, such as polymer materials, composite materials, ceramic materials, or concrete. The piezoelectric material particles may be used for evaluating the soundness of the structural member, such as in quality control, nondestructive testing, or structural health monitoring processes. The structural member may include one or more conductive pickups used for receiving signals from the structural member. The signals may be induced by introducing ultrasonic signals or vibrational resonance signals into the structural member. The response from such induced signals may be used for quality control purposes or structural health monitoring. The piezoelectric material particles may function to provide response signals from throughout the structural material, enabling easier evaluation of the soundness of the structural member. Piezomagnetic, magneto-strictive, or electro-strictive material particles may also be distributed throughout the structural material of the structural member, which serve to amplify and otherwise enhance the signals from the piezoelectric material particles. The piezoelectric, electro-strictive, magneto-strictive, and/or piezomagnetic material particles may allow the structural member to exhibit an electrical and/or magnetic response to forces on the structural member, such as accelerations. This may allow the structural member to function as a force sensor or an accelerometer. Signals induced by such external forces or accelerations may be taken from the conductive pickups and used for various operations, for example, for arming a warhead of a missile or for triggering passenger safety features such as air bags in automobiles.

Figure 1:
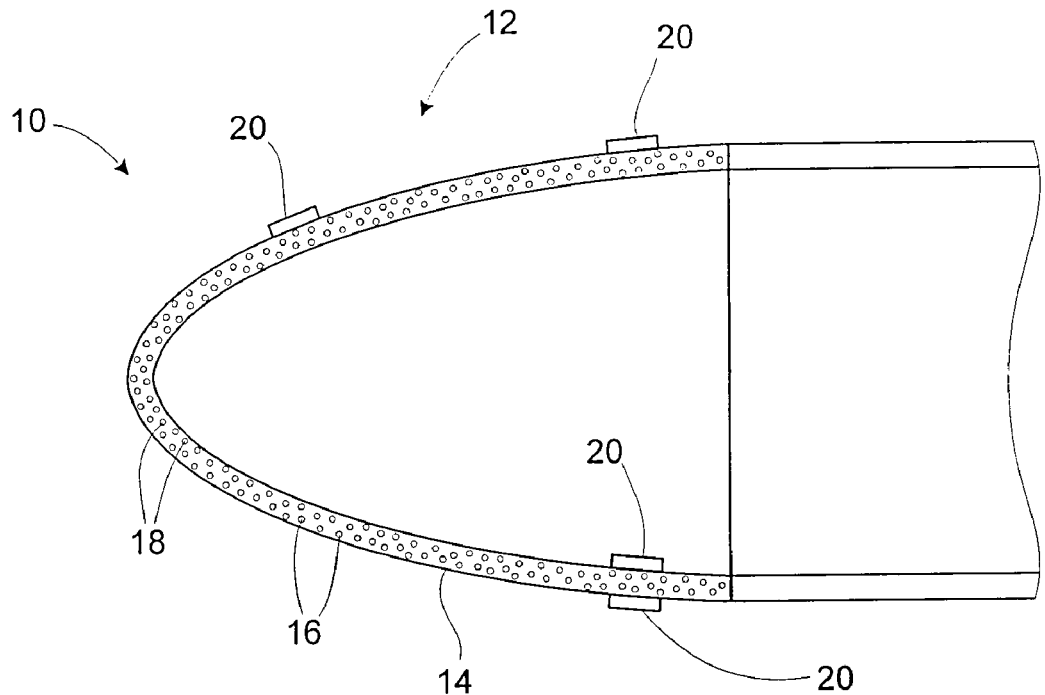
FIG. 1 is cross-sectional view of a structure in accordance with an embodiment of the present invention.

FIG. 1 shows a structure 10, a missile that includes a load-bearing structural member 12. In the illustrated embodiment, the structural member 12 is a nose cone of a missile, but it will be appreciated that the structural member 12 may be any of a wide variety of parts of any of a wide variety of structures.

The structural member 12 includes a continuous structural material 14 that has piezoelectric material particles 16, and electro-strictive, magneto-strictive, and/or piezomagnetic material particles, 18, mixed in throughout. The continuous structural material 14 may be any of a wide variety of structural materials, including polymer materials, composite materials, ceramics, and concrete. The structural material 14 provides a continuous structure for the load-bearing required of the structural member 12. The structural material 14 may be a composite material that includes sheets or other arrays of fibers. A composite material that is the continuous structure material 14 has an epoxy resin that may be hardened or cured, which serves as a continuous portion. Alternatively, the structural material 14 may be a liquid or gel that is hardened or cured to form a solid or viscoelastic material.

The piezoelectric material particles 16 may be lead zirconate titanate (PZT) particles. Suitable PZT particle powders are available from Morgan Electro Ceramics of Fairfield, N.J. The piezoelectric material particles 16 may have suitable sizes, for example being micron size or nanometer sized. Suitable amounts of piezoelectric particles may be added to the structural member 12, based on desired load characteristics, the material of the continuous structural material 14, and desired response characteristics, among other factors. Suitable weight fractions of the piezoelectric particles may range from on the order of 1 percent to as high as 40 percent of the material, depending on particle size, application, and the chemistry of the matrix material.

It will be appreciated that the volume of the piezoelectric material particles 16 and the electro-strictive, magneto-strictive, and/or piezomagnetic material particles 18 may be chosen so as to provide suitable signal strength without unduly degrading the material properties of the structural member 12.

The structural member 12 may also optionally include the electro-strictive, magneto-strictive, and/or piezomagnetic material particles 18. The piezomagnetic material particles 18 may be made of suitable magnetostrictive materials, such as a magnetostrictive alloy or magnetite (i.e. iron oxide). One suitable material is Terfenol-D, available in powder from ETREMA Products, Inc., of Ames, Iowa. The weight fraction of piezomagnetic material will be in the same range as given above for piezoelectric material. Likewise, if both piezoelectric and some combination of electro-strictive, magneto-strictive, and/or piezomagnetic particles are used in combination, then the combined weight fraction of the net particle mixture will be in the same range as listed above for piezoelectric particles.

The structural member 12 has one or more conductive materials, electrodes, or pickups 20. Various electrodes or pickups 20 may be located at various locations on the surface of or within the structural member 12. The electrodes or pickups 20 may be made of suitable conductive material, such as conductive metal foil, metallized fibers such as aluminized glass fiber, or conductive paint, for example silver paint. The pickups 20 may be used both for applying electrical fields to the structural member 12 in order to excite or drive the piezoelectric material particles 16 or pickup response signals from driving of the piezoelectric material particles 16.

Some of the pickups 20 may be used to create electric fields to drive the piezoelectric material particles 16, while other of the pickups 20 may be used to receive signals from the excitation of the piezoelectric material particles 16. Alternatively, the same pickup or pickups 20 may be used both for creating the fields, and for being monitored to examine the response of the structural member 12 to the induced fields. The excitation signal used to drive the piezoelectric material particles 16, for example, for quality control structural health monitoring, may be a periodic signal having a suitable frequency. Ultrasonic testing frequencies are typically in the range of several hundred kilohertz, to as high as hundreds of thousands of megahertz, with higher frequencies giving shorter wavelengths that enable the detection of smaller defect sizes. Vibrational resonance frequencies for structures typically range from the order of one to thousands of hertz, depending on the size of the structure and the vibrational harmonics that are excited. The electric field set up by the signal through the electrodes or pickups 20 causes stresses within the structural member 12, due to the forces generated by the electric field within the piezoelectric material particles 16. The piezomagnetic, electro-strictive, and/or magneto-strictive material particles 18 may amplify this effect and induce stresses of their own into the structural member 12.

Interpretation of response signals received at the same or another of the electrodes or pickups 20 may be used to characterize the mechanical soundness of the structural member 12. A simple example of interpretation of output signals would be to compare the output signal with previously obtained signals from known structurally sound parts or numerous examples presumed to be structurally sound. In ultrasonic testing this procedure is typically known as "producing a standard or reference." Output results that are similar to known or presumed sound parts would indicate a lack of structural defects. It would be expected that deviations in output signals from that of a sound part would indicate some sort of structural defect in a part, and the particular defects might be identified by further development of the reference standard. In addition, comparison may be made of output signals from the same structural member 12, taken at different times over the service life of the structural member. Development of a structural defect, even an internal structural defect, would be expected to cause deviation in output signal. Detection of these output signal deviations could be used to diagnose structural problems, even before the appearance of external indicators such as cracks. It will be appreciated that more complicated interpretation of output signals may be performed. For example, different types of signals may correspond to different types and/or locations of structural defects. Various correlations may be used to link various types of defects with various types of output signals. Such correlations may be based on examination of previous defective structures and/or may be based on theoretical or other predictive interpretations. Ultrasonic and vibrational testing methods based on the general approach of developing a reference standard have been used successfully in the past to test structural integrity, using conventional discrete external sensors. PMC (polymer matrix composite) fiber reinforcement disbands and delaminations have been detected using vibrational resonance techniques, while smaller, more localized defects have been detected ultrasonically using longitudinal, shear, surface, or interfacial wave modes. It will be appreciated that placement of the piezoelectric material particles 16 substantially uniformly mixed throughout the structural member 12 advantageously allows for examination of structural health of the entire structural member 12 (or a substantial part thereof substantially simultaneously. The individual piezoelectric material particles 16 in essence act as small signal generating devices, placed throughout the structural member 12. Rather than directing a single signal along a single direction within a structural member, as occurs when conventional discrete ultrasonic signal generation and reception sensors are used (such as piezoelectric transducers, thermoelastic or ablative laser generation, interferometeric or optical vibrational or ultrasonic reception, capacitance transducers, electromagnetic acoustic transducers, etc.), signals are induced volumetrically throughout the structural member 12. This advantageously may allow detection of defects in complex and difficult to characterize shapes because there are no "dead spots" inside the structure that cannot be readily reached, a problem which commonly occurs when using conventional discrete ultrasonic signal generation and reception sensors. Furthermore, because the methods described herein provide a volumetric source of vibrational and/or ultrasonic energy, signal interpretation for complex structures is also enhanced because signals can be received and analyzed before the arrival of spurious (i.e. back wall and side wall) echoes. The problem of spurious echoes often renders ultrasonic inspection of complex parts impossible when conventional generation and reception sensors are used.

The pickups 20 may have any of a wide variety of suitable configurations. As noted above, there may be only a single conductive electrode or pickup 20. Alternatively, there may be multiple pickups 20, for example being overlapped on opposite major faces of the structural member 12. It will be appreciated that a wide variety of ways of sending input signals and receiving output signals may be suitably accomplished. For example, output signals may be taken from different of the pickup 20 at different locations, to better characterize the structural health or soundness of the structural member 12. This is similar to what is commonly done today using conventional discrete signal generation and reception sensors. Similar or different signals may be input at individual of the multiple pickups or electrodes 20. In this manner either longitudinal, shear, surface, or interfacial waves may generated and received inside structural members, depending on the types of defects that are of interest.

It will be appreciated that the pickups 20 may be connected to suitable devices for generating and receiving signals. Among the suitable devices that the pickups or electrodes 20 may be coupled to are signal generators, spectrum analyzers, signal amplifiers and filters, pulse generators, and/or oscilloscopes. The specific details of a particular electronics array that might be used to generate and receive nondestructive testing signals, using the methods claimed here (i.e. the use of piezoelectric, piezomagnetic, electro-strictive, or magneto-strictive particles distributed throughout the structural material), would be quite similar to those that are already in common use today for the application of conventional signal generation and reception sensors. In the design and configuration of the driving and receiving electronics used for nondestructive testing and structural health monitoring purposes, the over arching goal is typically to maximize the overall signal to noise ratio (SNR). Likewise, it is to be understood that the particular mixture of piezoelectric, piezomagnetic, electro-strictive, and/or magneto-strictive particles that is used in any given specific application, will be chosen in such a way as to maximize the resultant SNR. The appropriate particle mixture may be chosen either based on experimental data, and/or analytical results.

The structural member 12 may also be monitored passively, without use of a specific electrical input signal. Forces on the structural member 12, such as stresses or accelerations, will produce forces within the continuous structural material 14. These will stress the piezoelectric material particles 16 and the piezomagnetic material particles 18, which will in turn create electric and magnetic fields. These fields may be detectable in output signals at the pickups or electrodes 20. These passive output signals may be used to determine accelerations or other events that produce forces within the structural member 12. Thus, the structural member 12 may be used itself as a sensor for sensing accelerations or other force-producing events. For example, the structural member 12 may function as a built in stress and/or strain indicator. Information received from monitoring of the output signals may be reported directly or may be used for triggering other functions. Similarly, the signals so generated could be used to detect impact events, for example a foreign object such as a bird striking the surface of an aircraft while in flight.

It will be appreciated that use of a structural material as an accelerometer for use as an arming device may be useful in other contexts, for example, in detonating warhead of a missile after penetration of an outer part of a target structure.

Figure 2:
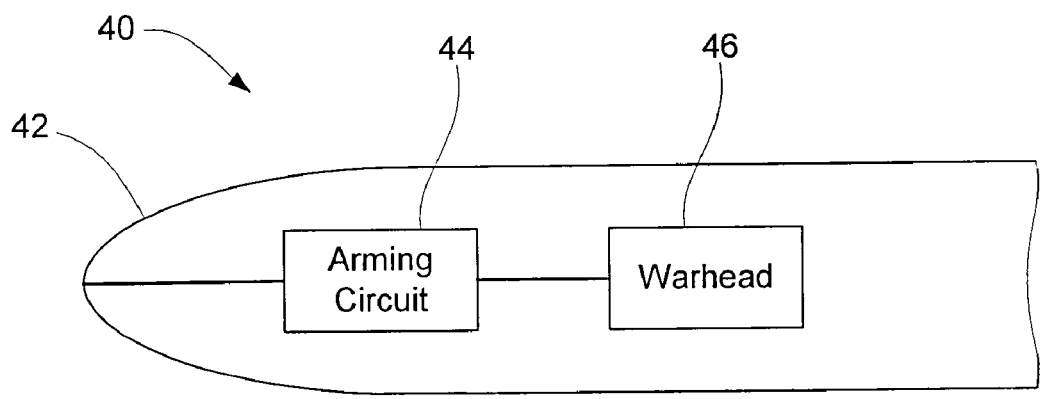
FIG. 2 is a schematic of a structure in accordance with another embodiment of the present invention.

One example of such triggering is illustrated in FIG. 2 where an output from a structural member 42 of a missile 40 is used to trigger an arming circuit 44 of the missile 40. This is used to arm a warhead 46 of the missile 40. The arming circuit 44 may be configured to act only when a signal is received from the structural member 42 indicating an acceleration corresponding to launch of the missile 40. Thus, the need for a separate accelerometer on a missile or other device may be dispensed with altogether.

Prior to measuring output from the structural member 12, the piezoelectric material particles 16 must be poled. This is done by subjecting the structural material 12 to a constant voltage of sufficient strength, at an elevated temperature, for a suitably long period of time. This poling aligns the piezoelectric material particles 16 (and the electro-strictive, magneto-strictive, and/or piezomagnetic material particles, 18 if present) such that there is similarity of orientation of the poles of the piezoelectric material particles. This allows achievement of similar responsiveness from different structural material samples.

Testing of several samples of structural members may be used to develop a baseline measurement for comparison of future similar structural members. It will be appreciated that the output response may be a function of many parameters, including configuration of the structural member 12, the type of material deployed as the continuous structural material 14, the material, size, and volume percentage of the piezoelectric material particles 16 and the piezomagnetic magnetic material particles 18, the location and configuration of the conductive electrodes or pickups 20, and the characteristics of the input signal.

The structural materials and methods described above may be used in a variety of different structures, from small conformal structures to very large structures. One advantage of the materials and methods is the ability to characterize structural soundness in a nondirectional manner, over essentially an entire structural member. Another advantage is a configuration that allows for essentially continuous monitoring of structural health throughout an entire structural member. A further advantage is the ability to have a built in way for evaluating health of a structural member without compromising uniform material properties within the structural member, and without having to apply external generation and reception sensors on the aerodynamic surfaces of aircraft.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method of detecting acceleration in a vehicle, the method comprising:
   placing at least one conductive pickup on a structural member of the vehicle, wherein the structural member includes a continuous structural material, and a plurality of piezoelectric, piezomagnetic, magneto-strictive, and/or electro-strictive material particles in the continuous structural material; and
   receiving electrical signals from the at least one conductive pickup, wherein the signals are indicative of electrical fields in the structural member caused by stresses induced in the structural member by acceleration of the vehicle.

2. The method of claim 1, wherein the detecting acceleration is used to control arming of a weapon.

3. The method of claim 1, wherein the placing includes placing a plurality of piezoelectric material particles in the continuous structural material.

4. The method of claim 3, further comprising exciting at least some of the piezoelectric material particles.

5. The method of claim 4, wherein the exciting includes subjecting the structural member to an ultrasonic signal.

6. The method of claim 4, wherein the exciting includes subjecting the structural member to a vibrational resonance signal.

7. The method of claim 4,
   wherein the placing also includes a plurality of piezomagnetic, electro-strictive, and/or magneto-strictive material particles in the continuous structural material; and
   wherein the exciting includes enhancing excitement of the piezoelectric material particles through the plurality of piezomagnetic, electro-strictive, and/or magneto-strictive material particles that are also in the continuous structural material.

8. The method of claim 1, wherein the placing includes placing a plurality of piezomagnetic material particles in the continuous structural material.

9. The method of claim 1, wherein the placing includes placing a plurality of electro-strictive material particles in the continuous structural material.

10. The method of claim 1, wherein the placing includes placing a plurality of magneto-strictive material particles in the continuous structural material.

11. The method of claim 1, further comprising selectively triggering one or more events based on the electrical signals.

12. The method of claim 11, wherein the selectively triggering includes selectively arming a warhead based on the electrical signals.

13. The method of claim 12, wherein the selectively arming includes sending an arming signal to an arming circuit.

14. The method of claim 11, wherein the selectively triggering includes selectively detonating a warhead based on the electrical signals.

15. The method of claim 11, wherein the selectively triggering includes triggering one or more passenger safety features based on the electrical signals.

16. The method of claim 15, wherein the one or more passenger safety features include air bags.

17. The method of claim 1, further comprising detecting impact events by monitoring the electrical signals.

18. The method of claim 1, wherein the placing the at least one conductive pickup includes placing multiple conductive pickups placed at different respective locations on the structural member.

19. The method of claim 1, wherein the placing the at least one conductive pickup includes placing a conductive foil pickup on a surface of the structural member.

20. The method of claim 1, wherein the placing the at least one conductive pickup includes placing a conductive paint pickup on a surface of the structural member.

* * * * *